Nov. 22, 1960 | C. C. BRUNES | Plant Pat. 1,989

STRAWBERRY PLANT

Filed Feb. 20, 1958 | 2 Sheets-Sheet 1

INVENTOR
CHARLES C. BRUNES
BY
Williamson, Schroeder, Adams & Palmatier
ATTORNEYS United States Patent Office Plant Pat. 1,989
Patented Nov. 22, 1960

1,989

STRAWBERRY PLANT

Charles C. Brunes, Pequot Lakes, Minn.

Filed Feb. 20, 1958, Ser. No. 716,520

1 Claim. (Cl. 47—62)

My discovery relates to a new and distinct variety of strawberry plant which is the result of a seedling found in a cultivated area and believed to be a found seedling of the Brunes Marvel strawberry (an unpatented variety well known in Northern Midwestern States of the United States).

The mother plant was grown and discovered in my cultivated strawberry fields at Pequot Lakes, Minnesota, and I have asexually reproduced a large number of plants of this new variety in my fields from the original mother plant by transplating rooted runner plants thereof.

My new variety winters well and is hardier than the Brunes Marvel and the Red Rich strawberry plant of Plant Patent No. 993. It also has good disease and insect resistance. The leaves of the plant are resistant to "leaf roller" and "leaf hopper" insects. My plant is immune from insects known as "yellows" and resistant to "leaf spot." On my strawberry ranch, many different types of strawberries have been grown throughout the last three seasons including those covered by Plant Patent 993 and Plant Patent 1,183. I made careful observation of all of the strawberry plants grown on my ranch during the past three seasons to detect leaf damage from common diseases known as yellows and leaf spot and such observation showed that the leaves of my plants were immune to "yellows" and highly resistant to "leaf spot" whereas the other plants' leaves were substantially affected by such diseases. The same observation of all of the plants showed that insects including "leaf roller" and "leaf hopper" had little effect upon the leaves of my improved plants.

The berry itself is larger than the Brunes Marvel and has a sweet, non-acid flavor throughout and is firm and of good keeping and shipping qualities. The berries vary in shape from a sharply wedged berry to a somewhat flat oval or conical shaped berry, and has a uniform color throughout with little, if any, core. The central portion of the berry is substantially solid throughout. The berry is particularly characterized by its good size, firmness and delicious, sweet, non-acid flavor. My new variety starts blooming about May 15th in the north for the June crop, and continuous until about June 5th. The first berries for the June crop appear about June 15th, and the date of the last berries for the June crop is about July 4th. The first blossoms for the second crop appear about June 25th and the crop begins its bearing about July 15th on spring planting, and continues to bear until the first fall killing frost.

In the accompanying drawing groups of typical berries are illustrated, and also a plant growing in the field with berries and blossoms thereon. In said drawings.

Figure 1:
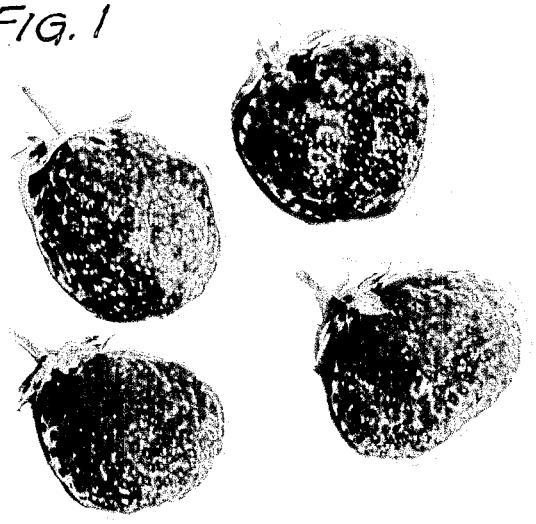
Fig. 1 is an external perspective view of a group of typical strawberries of my invention.
Figure 2:
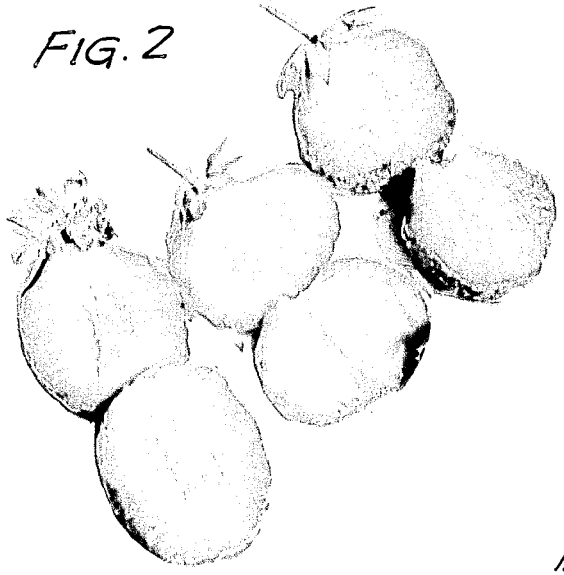
Fig. 2 is a perspective view of a group of typical strawberries of my invention which have been stem-sliced to show the interiors in section.
Figure 3:
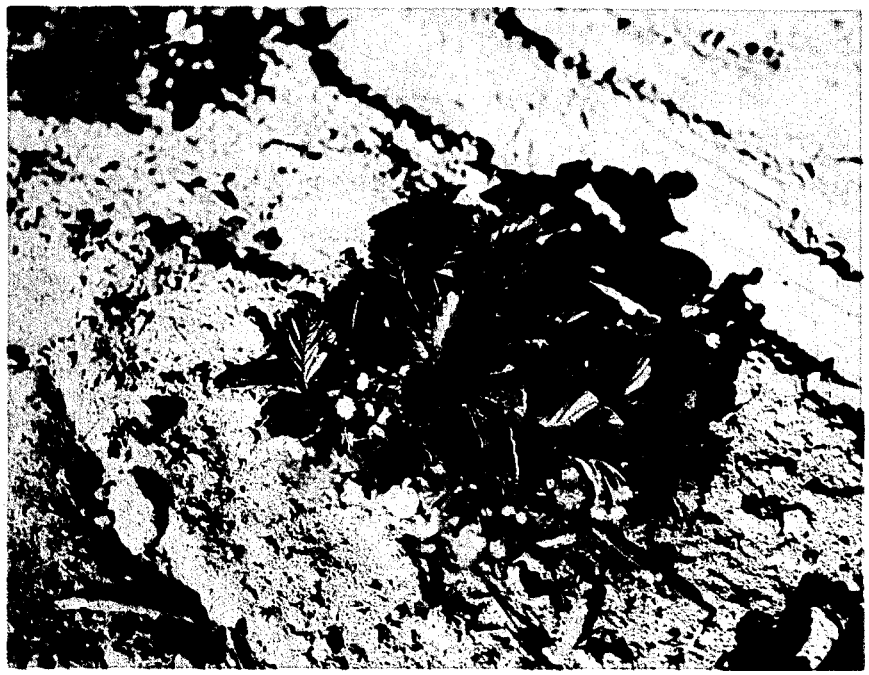
Fig. 3 is a perspective view of a typical plant growing in the field with berries and blossoms thereon.

As a convenient summary, the following is a detailed description of this new variety of strawberry plant:

*Plant characteristics*

*Size.*—Medium to large roots, thick and relatively long root system.

*Crown size.*—Larger than most strawberry plants including the crown size of the plants in Plant Patents 1,183 and 993, excellent crown size relative to leaf size (produces hardy plant).

*Leaves.*—Similar to Brunes Marvel (not a patented variety), generally trifoliate, but four or five leaflets on a single petiole are not uncommon.

*Petiole.*—Generally similar to but more slender than those of the Brunes Marvel and those of Plant Patents 1,183 and 993.

*Leaflets.*—Generally rounded periphery with substantially uniform serrations. The leaflets are somewhat longer than they are broad, and are generally cupped slightly upwardly, similar to the Brunes Marvel and are less cupped than the leaves of the plants in Plant Patents 1,183 and 993. The upper surface of the leaf is smooth and has a dark green color, and the lower surface has medium pubescence, and is lighter green in color.

*Runners.*—Heavy tendrils, larger than most strawberry plants, and somewhat larger than the Brunes Marvel. Approximately six runners are produced on each plant during the growing season, and each of these runners bears well and matures quickly during the season.

*Flower stems.*—Thick, generally upright, and partially exposed.

*Flowers.*—Blossoms are perfect and relatively large, as contrasted with the blossoms of Plant Patents 1,183 and 993. Nearly all blossoms produce salable fruit. They are self-pollinizing.

*Sex.*—Bisexual.

*Soil.*—Plants grow well in poor sandy type soils, and have a good root system.

*Frost-resistance.*—Very hardy and excellent resistance to frost damage in typical Northern United States climate where humidity during the months of August through October averages over 40% and frosts are frequent after October 15th.

*Resistance to excessive moisture and rain.*—Apparently good.

*Drouth resistance.*—Excellent.

*Fruit characteristics*

*Condition.*—Prime, during the substantially entire growing season.

*Size.*—Somewhat larger than the Brunes Marvel and the fruit of Patents 1,183 and 993, Lengths (major axis) average 1⅝".

*Surface contour.*—More regular than most strawberries.

*Shape.*—Varies—some berries wedge shaped, others, somewhat flat oval in shape, and others somewhat conical.

*Fruit stems.*—Similar to Brunes Marvel—somewhat longer than most strawberries including the fruit stems of Plant Patents 1,183 and 993, thus holding the berries well above the foliage for exposure to sunlight and providing for easier picking.

*Aspect and color.*—Very glossy, uniform intense red color throughout the entire exterior of the berry, said color as illustrated in "Dictionary of Color" by Merz and Paul, published by McGraw Hill Book Company Inc., second edition, being shown in vertical column L of plate 5 page 33 of said dictionary, varying in color intensity between areas 3 and 6 horizontal column, the center of my ripened berries are of a rather uniform red color slightly lighter than the deep red of the exterior and as illustrated in said above identified, authoritative Dictionary of Color, being shown in plate 2, page 27, the color varying in horizontal column 10 from vertical column C to vertical column J. The external red color is darker and more intense than the color of the fruit of Plant Patent 1,183 and is as intense but slightly lighter in the shade of red than the fruit of Plant Patent 993.

*Seeds.*—Shy seeder. Seeds are flush and bright.

*Core.*—Substantially no core, center of berry firm, and has a color substantially the same as the outer portion of the berry flesh.

*Calyx.*—Small, tight against the berry surface; very scant pubescence.

*Flesh.*—Juicy and extremely firm; resistant to shipping damage to the extent that ordinary travel without refrigeration to the extent of two days time under temperature conditions above 70 degrees, will not spoil or damage the berries.

*Flavor.*—Very sweet—non-acid taste, apparently has a high sugar content (requires less sugar than most berries for eating, preserving and freezing).

*Uses.*—Extremely good dessert quality, also good for canning and freezing.

The strawberry described above, and the plant producing the same may vary in slight details, depending upon weather conditions and soil conditions under which they are grown.

What I claim is:

A new and distinct variety of everbearing strawberry plant substantially as herein shown and described, characterized by a very sweet, non-acid flavor of the fruit, said fruit having very firm flesh throughout and having a uniform and intense exterior darkish red color within the range described herein and with substantially no core in the fruit and with the color of the interior of the fruit being only slightly lighter than said external color and within the color range described herein, said plant being hardy with heavy root structure and long runners which mature quickly and bear well throughout the growing season, the fruit having unusually long stems and said plants bearing substantially continuously throughout the season and producing a full and excellent yield.

References Cited in the file of this patent

UNITED STATES PATENTS

P.P. 1,183 Keplinger ---------- May 5, 1953